US006172746B1

(12) United States Patent
Byrne et al.

(10) Patent No.: US 6,172,746 B1
(45) Date of Patent: Jan. 9, 2001

(54) TRANSMITTED LIGHT REFRACTOMETER

(75) Inventors: Michael J. Byrne, East Aurora; Thomas E. Ryan, Batavia; Kyle R. Bleyle; Keshav D. Sharma, both of Lancaster; Robert C. Atkinson, Buffalo; David J. Cash, Kenmore, all of NY (US)

(73) Assignee: Leica Microsystems Inc., Depew, NY (US)

( * ) Notice: Under 35 U.S.C. 154(b), the term of this patent shall be extended for 0 days.

(21) Appl. No.: 09/429,123

(22) Filed: Oct. 27, 1999

(51) Int. Cl.[7] .................................................. G01N 21/41
(52) U.S. Cl. ............................................ 356/135; 356/137
(58) Field of Search ..................................... 356/128, 129, 356/130, 131, 132, 133, 134, 135, 136, 137

(56) References Cited

U.S. PATENT DOCUMENTS

| 2,966,091 | * | 12/1960 | Goldberg | 356/136 |
| 3,625,620 | * | 12/1971 | Goldberg | 356/135 |
| 4,188,116 | * | 2/1980 | Rartfay-Szabo | 356/137 |
| 4,243,321 | * | 1/1981 | Okuka et al. | 356/135 |
| 4,640,616 | | 2/1987 | Michalik | 356/136 |
| 5,969,808 | * | 10/1999 | Cotton et al. | 356/135 |

OTHER PUBLICATIONS

LEICA ABBE MARK II Refractometer, Model 10480/10481/10494/10495—Instruction Manual—Copyright 1997.

* cited by examiner

Primary Examiner—Hoa Q. Pham
(74) Attorney, Agent, or Firm—Simpson, Simpson & Snyder, L.L.P.

(57) ABSTRACT

A transmitted light refractometer comprises an optical system having a movable mirror for redirecting light transmitted through a light-refracting sample to a beam splitter for dividing the light between first and second detection paths. The first detection path leads to an eyepiece whereby an operator may view an illumination boundary shadowline brought into the field of view of the eyepiece by adjusting the position of the movable mirror. The second detection path leads to a light-sensitive detector, preferably a linear scanned array, for generating signal information indicative of the location of the shadowline on the detector. An optical position sensor associated with the movable mirror includes a position detector providing signal information indicative of the position of the movable mirror. During a reading, the shadowline is brought into the field of view of the eyepiece, and the shadowline signal information and the mirror position signal information are processed to calculate index of refraction of the sample.

8 Claims, 12 Drawing Sheets

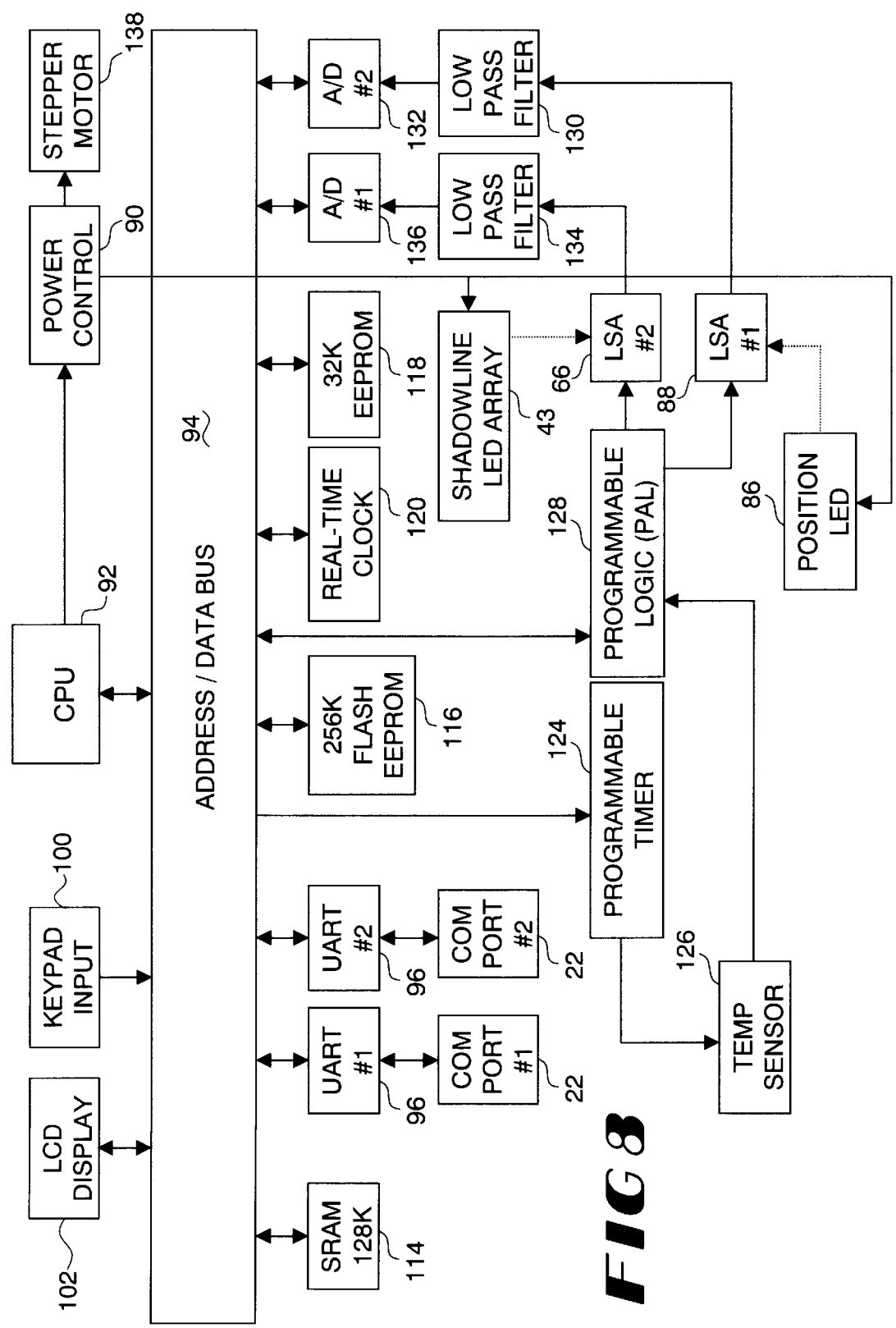

TRANSMITTED LIGHT REFRACTOMETER

BACKGROUND OF THE INVENTION

A. Field of the Invention

The present invention relates to the field of refractometers for measuring the refractive index of a sample, and more particularly to an automated transmitted light refractometer that reduces operator influence on the measurement taken.

B. Description of the Prior Art

Abbe refractometers are widely used for measuring the refractive index of liquid samples. Prior art Abbe refractometers are known to comprise a mirror movable relative to a light-transmitting prism assembly on which a sample is placed, such that a critical angle dependent shadowline is viewable through an eyepiece by adjusting the orientation or position of the mirror redirecting the transmitted light. With such instruments, the operator must adjust an externally mounted illumination source relative to the prism assembly and visually align the shadowline with a crosshair or other reference marking by adjusting the mirror. A reading of refractive index is based on the mirror position as determined by a motorized gauge which runs each time a reading is taken. The step of visually aligning a crosshair to a reference introduces human error, particularly among different operators. Also, the use of a motorized gauge for determining mirror position causes a delay in reporting the reading.

U.S. Pat. No. 4,640,616 teaches an automatic reflected light refractometer in which the various optical elements defining the instrument's optical path are fixed relative to one another. The optical path leads to a linear scanned array, as opposed to an operator's eye, to detect the location of a shadowline for calculating refractive index. The instrument described in the patent measures a relatively small range of refractive indices as compared with refractometers having a movable mirror, and is without a manual mode.

SUMMARY OF THE INVENTION

It is therefore an object of the present invention to provide an improved transmitted light refractometer that eliminates the need for an operator to manually adjust shadowline position until the shadowline is aligned with a reference marker as viewed by the operator during a sample reading.

It is another object of the present invention to provide an improved transmitted light refractometer that can instantaneously determine the position of a movable mirror of the refractometer.

It is a further object of the present invention to provide an improved transmitted light refractometer that incorporates an internal fixed illumination source to eliminate the need for adjustment.

It is a further object of the present invention to provide an improved transmitted light refractometer that can be adjusted to any of a very large number of viewable ranges.

It is a further object of the present invention to provide an improved transmitted light refractometer that can be easily upgraded from semi-automatic to fully automatic through its entire range if desired.

It is yet a further object of the present invention to provide an improved transmitted light refractometer that incorporates a second illumination source for reflected light refractometry in addition to transmitted light refractometry.

In view of these and other objects, a refractometer formed in accordance with the present invention includes an elevator assembly for adjustably supporting a movable optical element relative to a light-transmitting prism assembly on which the sample is placed. A beam splitter is located downstream from the movable optical element to divide light between a pair of detection paths, the first detection path leading to an eyepiece and the second leading to a light-sensitive shadowline detector, whereby the refractometer can function in automatic or manual modes. The elevator assembly includes a position light source traveling with the movable optical element and cooperating with a position detector for instantaneously providing signal information indicative of the position of the movable optical element. In a preferred embodiment, both the position detector and shadowline detector are identical linear scanned arrays. The output from both detectors is converted to digital form and processed using stored relationships between refractive index and detector cell numbers, as well as calibration offsets and magnification factors, to arrive at sample refractive index.

BRIEF DESCRIPTION OF THE DRAWINGS

The nature and mode of operation of the present invention will now be more fully described in the a following detailed description of the preferred embodiments taken with the accompanying drawing figures, in which:

FIG. 8 is an electronic block diagram showing circuitry of the refractometer shown in FIG. 1;

DETAILED DESCRIPTION OF THE PREFERRED EMBODIMENT

Figure 1:
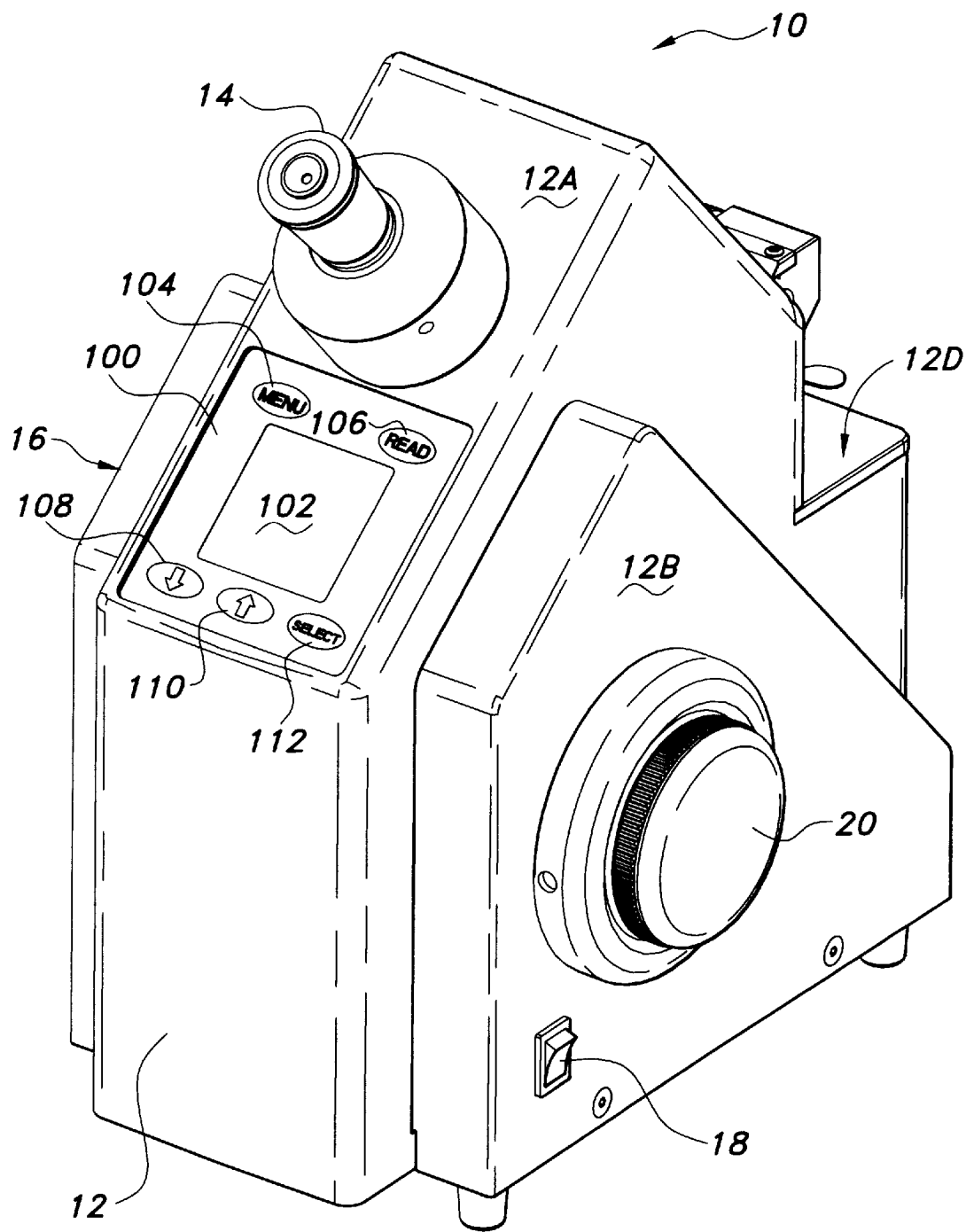
FIG. 1 is a front perspective view of a transmitted light refractometer formed in accordance with a preferred embodiment of the present invention.
Figure 2:
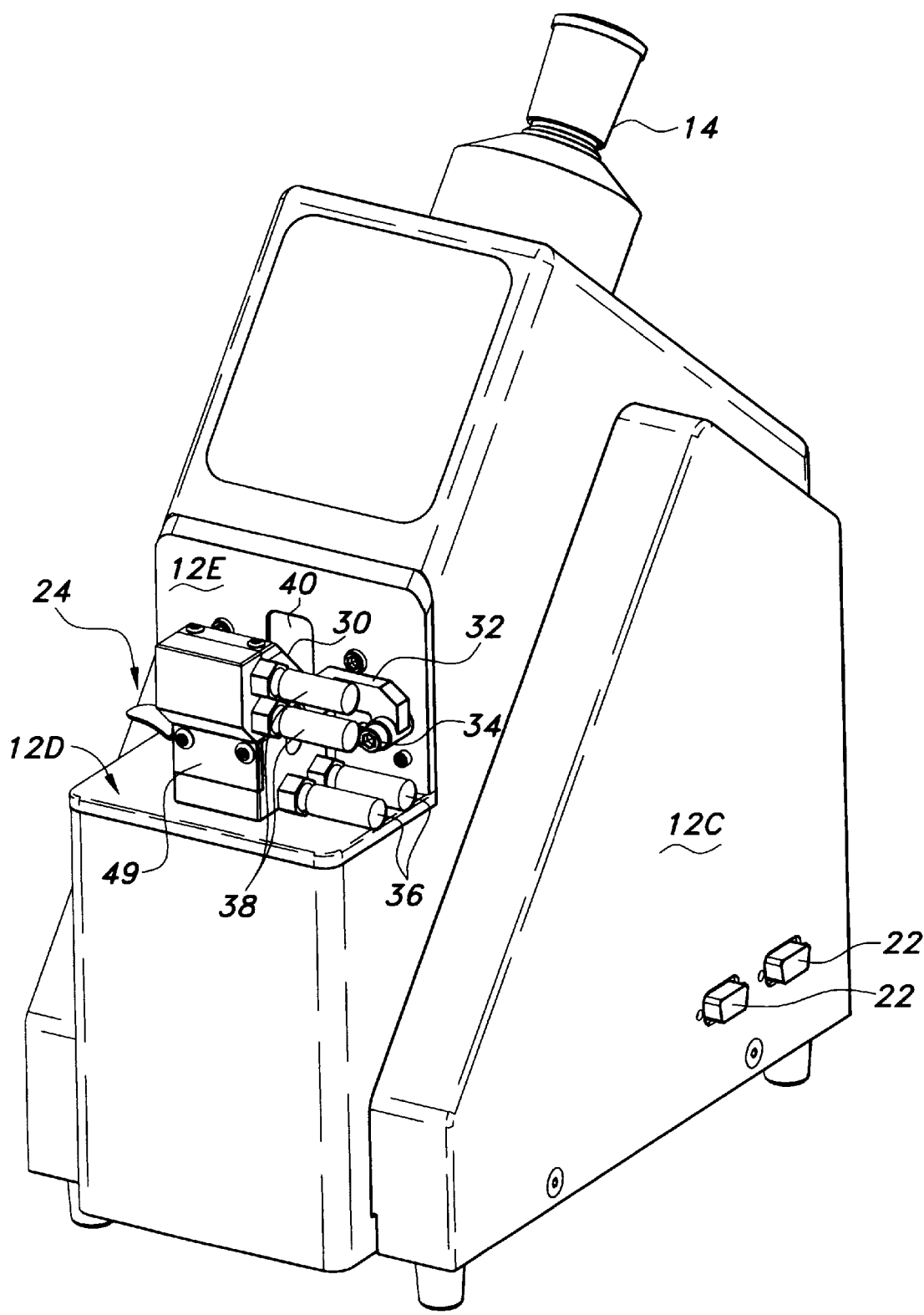
FIG. 2 is a rear perspective view of the refractometer shown in FIG. 1.

Referring initially to FIGS. 1 and 2 of the drawings, a transmitted light refractometer formed in accordance with a preferred embodiment of the present invention is shown and identified generally by the reference numeral 10. Refractometer 10 is used to measure the refractive index of a light-transmitting sample substance, and reports such measurement in terms of D-line refractive index, percent solids, and temperature compensated values of same. Refractometer 10 is shown as comprising a housing 12 having a sloped front surface 12A, right and left opposite side panels 12B and 12C, a horizontal rear surface 12D and an upstanding rear surface 12E intersecting with horizontal rear surface 12D. A focusable eyepiece 14 extends upwardly and forwardly from sloped front surface 12A, and an electronic user interface 16 is situated on front surface 12A just below eyepiece 14. A power switch 18 and a rotatable shadowline adjustment knob 20 are provided on right side panel 12B. A pair of RS232 serial communication ports 22 is located on left side panel 12C.

Figure 4:
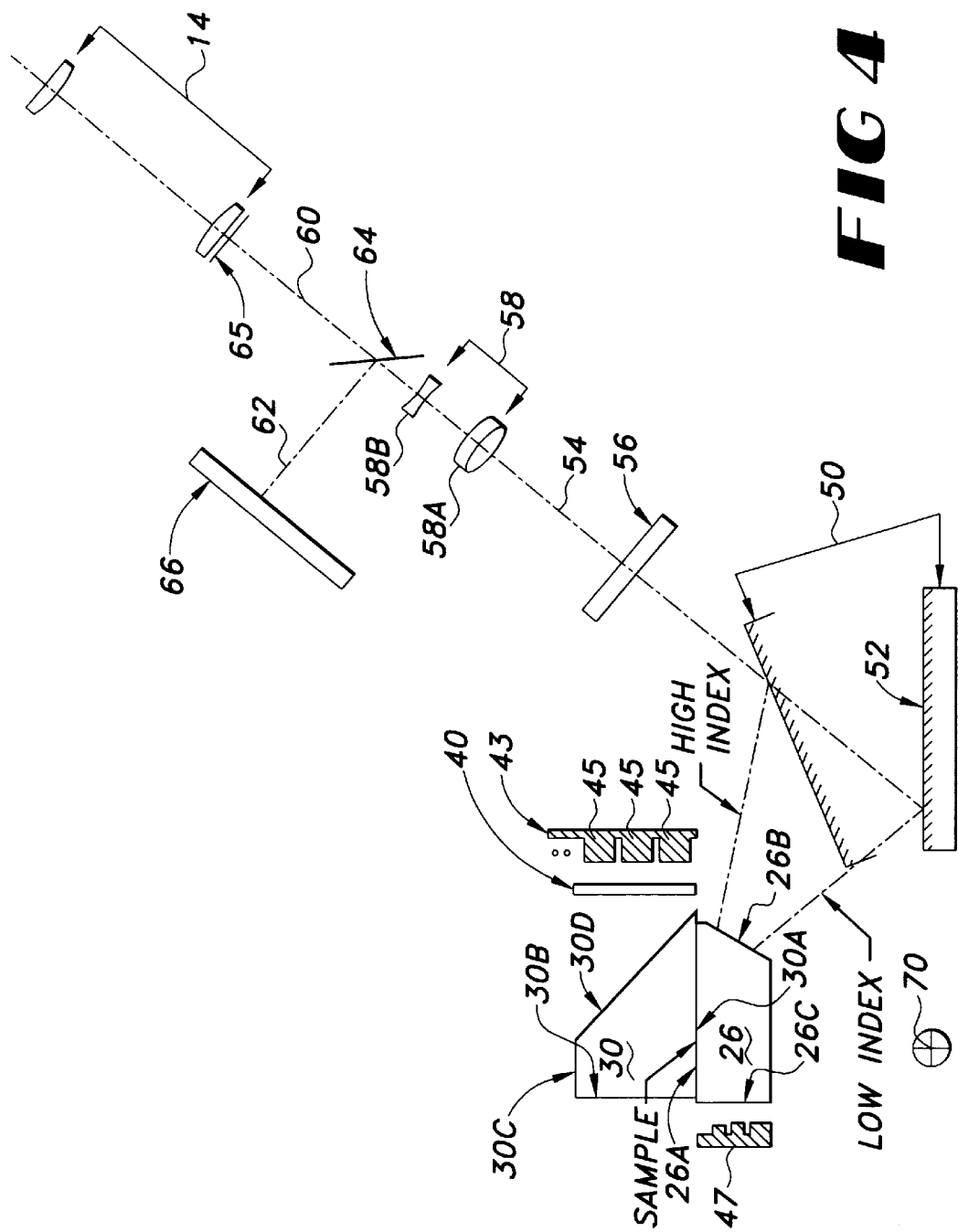
FIG. 4 is a schematic diagram showing an optical system thereof.

Refractometer 10 further comprises a prism assembly 24 exposed above horizontal rear surface 12D for receiving a light-transmitting sample substance for testing purposes. As best seen in FIG. 4, prism assembly 24 includes a refraction prism 26 having an upper horizontal entry face 26A for receiving the sample. Prism assembly 24 also includes an illumination prism 30 mounted at a distal end of a pivot arm 32 for rotation about an axis defined by a pivot pin 34 which pivotably connects a proximal end of the pivot arm to upstanding rear surface 12E. As can be understood, illumination prism 30 is pivoted away from refraction prism 26 to allow an operator to add a sample substance to sample-receiving entry face 26A of refraction prism 26, and is pivoted in a reverse direction once the sample has been added such that the sample is confined between opposing faces of refraction prism 26 and illumination prism 30. Two water bath ports 36 are provided adjacent refraction prism 26 and another two water bath ports 38 are provided adjacent illumination prism 30 to enable communication with a commercially available water bath to circulate fluid at a predetermined temperature for regulating the temperature of refraction prism 26 and illumination prism 30, as is well known in the art of refractometry. Finally, an illumination window 40 is located in upstanding rear surface 12E opposite from illumination prism 30.

Figure 3:
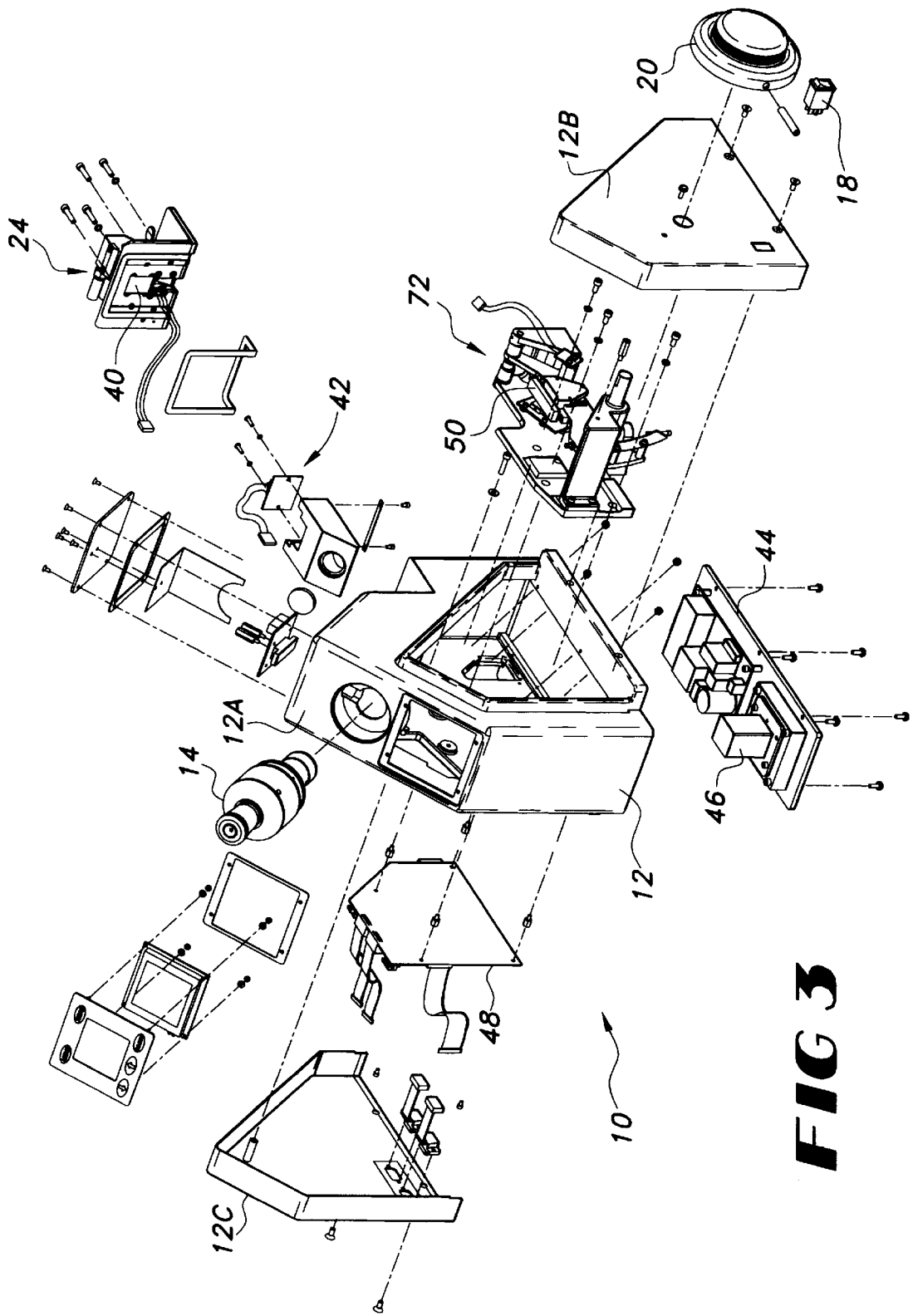
FIG. 3 is an exploded perspective view thereof.

FIG. 3 is an exploded view showing internal components of refractometer 10 mounted within housing 12. Among the internal components of refractometer 10 are an illumination source 42 arranged to transmit light through illumination window 40, a base assembly 44 supporting a power supply 46, an upstanding main electronic logic board 48 adjacent left side panel 12C, a movable optical element 50, and an elevator assembly 72.

FIG. 4 schematically illustrates the optical configuration of refractometer 10. Illumination source 42 preferably comprises an area array 43 made up of a plurality of light emitting diodes (LEDs) 45 arranged to direct light through illumination window 40 to illumination prism 30. By way of example, area array 43 can be chosen as a two-by-three array of LEDs 45 emitting light having a nominal wavelength of 589 nm. Illumination prism 30 which receives the light from LED area array 43 includes an exit face 30A, an internally reflective surface 30B acutely angled at 45° with respect to exit face 30A, a top face 30C parallel to exit face 30A, and an entry face 30D joined at right angles to top face 30C and exit face 30A. Illumination prism 30 is preferably formed of Schott SF11 glass having a nominal refractive index of 1.79190 at 589 nm. All surfaces of illumination prism 30 other than entry face 30D and exit face 30A are coated with a reflective coating, preferably protective aluminum with silicon dioxide, and protective black paint is applied to these coated surfaces. As will be understood, light from LED area array 43 enters illumination prism 30 at entry face 30D and is trapped for internal reflection by the coated surfaces until it exits illumination prism 30 through exit face 30A as an illumination field of diffuse light.

Refraction prism 26 is shown as including entry face 26A opposite exit face 30A of illumination prism 30, an exit face 26B acutely angled at 60° with respect to entry face 26A, and a back face 26C extending at a 90° angle from entry face 26A. Refraction prism 26 is preferably formed of Schott LaF22A glass having a nominal refractive index of 1.78677 at 589 nm. All surfaces of refraction prism 26 other than entry face 26A and exit face 26B are painted with dead flat black enamel paint to effectively eliminate unwanted internal reflection and entry of stray light. The fluid sample to be tested is confined between exit surface 30A above and parallel entry surface 26A below when the system is set for testing.

As an optional feature, an additional illumination source 47 can be positioned to direct light though back face 26C to sample/entry face 26A for conducting reflected light refractometry. Face plate 49, seen in FIG. 2, is removable for this purpose, and back face 26C is left unpainted if this option is desired.

A field of diffuse illuminating light is transmitted by the sample and is obliquely incident to entry face 26A. Light incident at angles less than the critical angle is refracted as it passes from the sample medium to the refraction prism medium of higher index, while light incident at angles greater than the critical angle is reflected by entry face 26A, such that a sharp and observable boundary line is defined by light leaving refraction prism 26 through exit face 26B. The angle at which this boundary or "shadowline" occurs allows for determination of the critical angle and hence the unknown refractive index of the sample.

Movable optical element 50, most preferably a mirror having a reflecting surface 52, is arranged to receive the transmitted light and reflect it along a detection path portion 54 having a 589 nm filter 56 and a collimating lens system 58 aligned thereon. Collimating lens system 58, by way of example, includes an achromatic positive doublet 58A followed by a biconcave lens 58B.

In accordance with the present invention, detection path portion 54 can be thought of as comprising coincident legs of first and second detection paths 60 and 62 defined by a beam splitter 64 orientated at a 45° angle with respect to detection path portion 54 after collimating lens system 58. Thus, first detection path 60 is followed by light that is transmitted through beam splitter 64 toward eyepiece 14, while second detection path 62 is followed by light reflected by beam splitter 64 toward a light-sensitive detector 66. It will be appreciated that the collimated light imaged at both the operator's eye 67 and at detector 66 defines a shadowline at the boundary between an illuminated area and an adjacent dark area. A crosshair reticle 65 is positioned on first detection path 60 before eyepiece 14 for presenting a crosshair image to the operator used to establish a measurement reference position for the shadowline as will be described hereinbelow. A shadowline detector is a SONY ILX 505A linear scanned array having 2624 cells, however other photoelectric detection devices can be employed without straying from the present invention.

Figure 5:
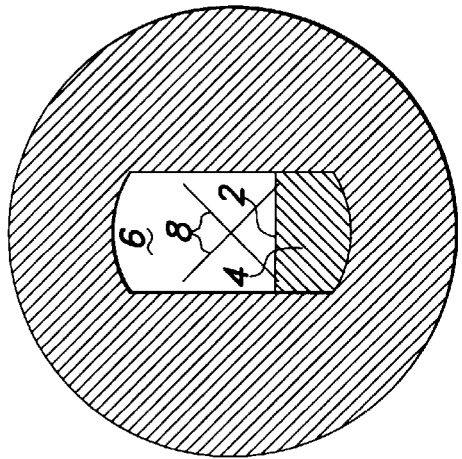
FIG. 5 shows a measurement shadowline and reference crosshairs as viewed by an operator of the refractometer.

FIG. 5 is a view showing what an operator might see when looking through eyepiece 14. A shadowline 2 is defined by the boundary between a dark area 4 and an illuminated area 6. An image of reference crosshairs 8 intersecting at a central point in the field of view is produced by crosshair reticle 65.

Since the direction of light leaving exit face 26B of refraction prism 26 varies with the sample refractive index, optical element 50 is movable with respect to exit surface 26B for adjusting the angle of incident light to enable light to be redirected by optical element 50 so that the aforementioned shadowline appears in the field of view of eyepiece 14, as shown in FIG. 5, and in the field of view of shadowline detector 66. In the embodiment shown, reflecting surface 52 is rotatable about a horizontal adjustment axis 70 through an angular range to accommodate different samples having a refractive index within a range of about 1.3 through about 1.7. The range of motion is indicated schematically by the alternate position phantom line depiction of optical element 50.

Figure 6:
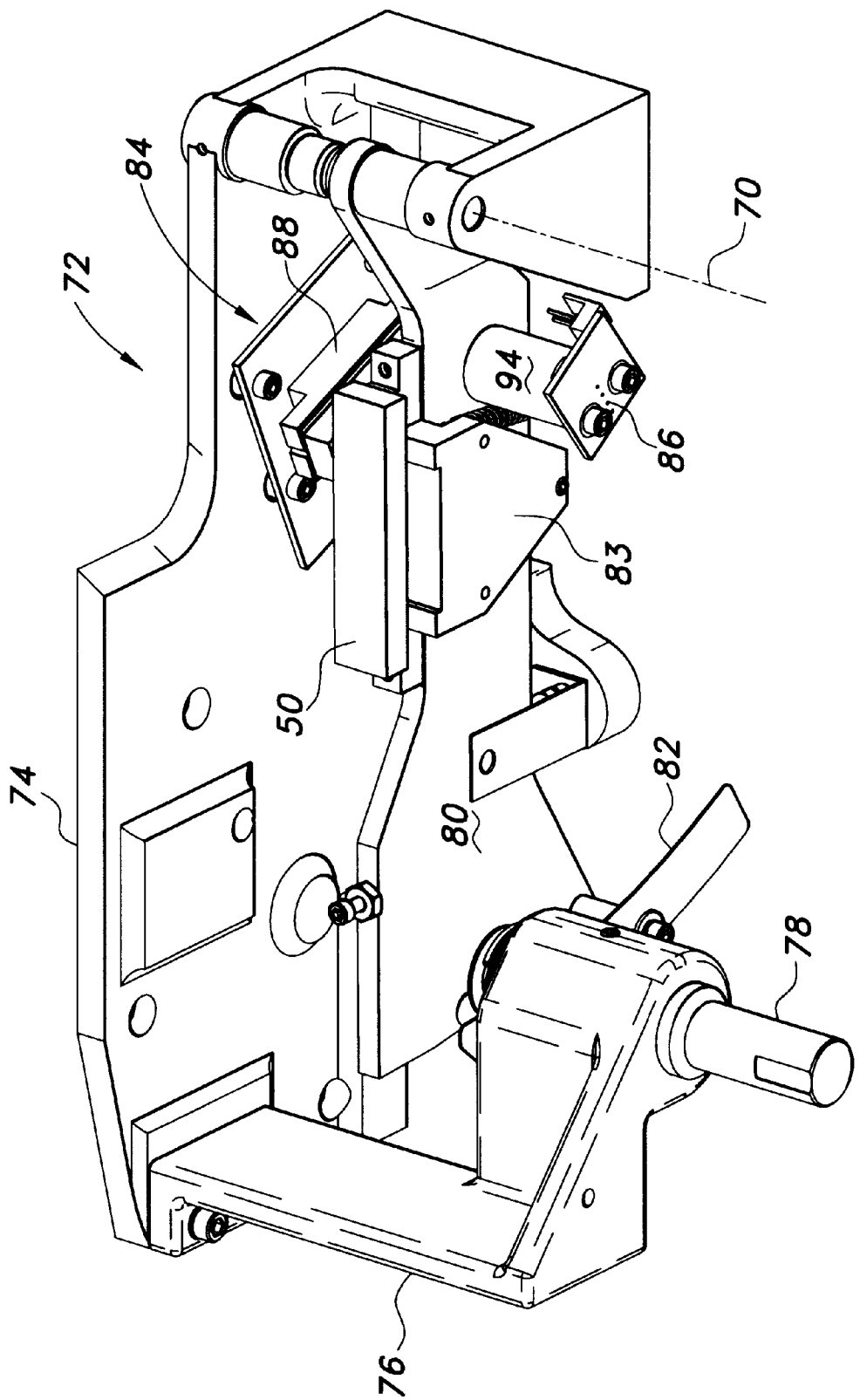
FIG. 6 is a perspective view showing an elevator assembly of the refractometer.
Figure 7:
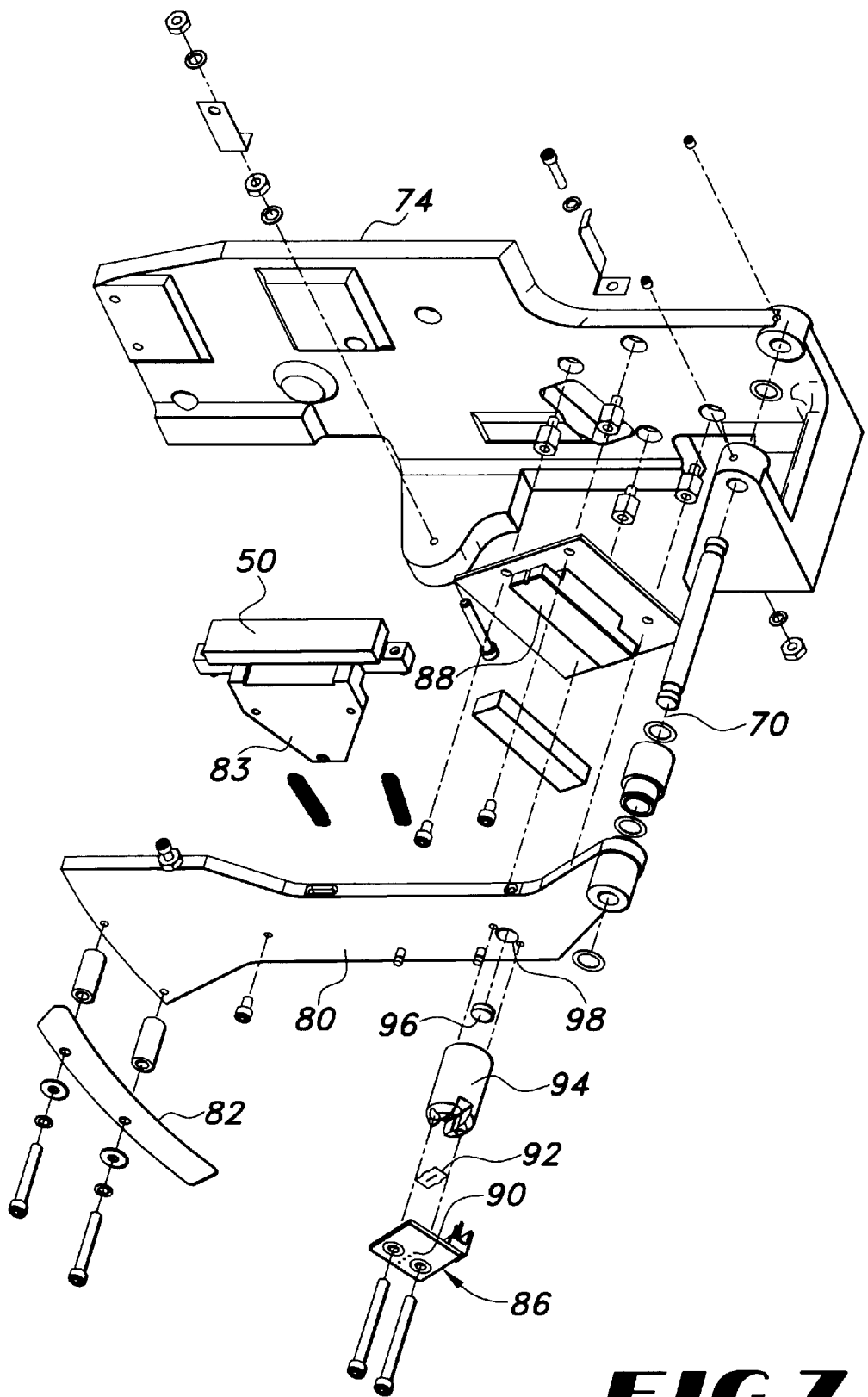
FIG. 7 is an exploded perspective view showing a portion of the elevator assembly shown in FIG. 6.

Referring also now to FIGS. 6 and 7, movable optical element 50 is preferably mounted for manually controlled rotation about adjustment axis 70 by elevator assembly 72 contained within housing 12 and operably coupled to external adjustment knob 20. Elevator assembly 72 generally includes a support plate 74 that is fixedly attached to an inner surface of left side panel 12C, an L-shaped adjustment mount 76 fixed to an end of support plate 74 opposite from adjustment axis 70, a clutch shaft 78 pivotally supported by adjustment mount 76, and an elevator arm 80 pivotally mounted at a first end thereof to support plate 74 for rotation about adjustment axis 70 and operatively coupled at a second end thereof to clutch shaft 78 by way of an arcuate adjustment blade 82. An end of clutch shaft 78 extends through right side panel 12B and is connected to adjustment knob 20, whereby rotation of adjustment knob 20 is transmitted to adjustment blade 82 to force rotation of elevator arm 80 about adjustment axis 70. Movable optical element 50 is mounted on a bracket 82 fixed to a mid-portion of elevator arm 80 such that movable optical element 50 is carried by elevator arm 80.

Elevator assembly 72 further includes position sensing means 84 for providing electronic signal information indicative of the position of movable optical element as it rotates about adjustment axis 70. In the embodiment shown, position sensing means 84 comprises a position light source 86 fixedly mounted to elevator arm 80 for travel with movable optical element 50 relative to a light-sensitive position detector 88 fixed to support plate 74. Position light source 86 preferably includes a linear source made up of a straight row of LEDs 90 facing a slit aperture 92 attached to the end of a hollow position mount 94 on elevator arm 80. Other position light sources are of course possible, including point sources or laser diodes. Position mount 94 is aligned with a position lens 96 set within a hole 98 through elevator arm 80 such that light from position light source 86 is directed through the elevator arm and focused on position detector 88. As with the shadowline detector, a preferred position detector is a SONY ILX 505A linear scanned array having 2624 cells, however other photoelectric detection devices are possible. It will be appreciated that an alternative arrangement is possible wherein light-sensitive position detector 88 is mounted on elevator arm 80 for travel with movable optical element 50, and position light source 86 is fixed to support plate 74. In either arrangement, the position light source 86 and position detector 88 cooperate to provide signal information relatable to the position of movable optical element 50 based on which element or cell of the position detector is aligned with the position light source so as to generate a peak output signal.

Accordingly, in the present invention, there are two detector arrays for generating signal information describing the refractive optical system, namely position detector 88 and shadowline detector 66. When refractometer 10 is in its automatic mode, the signal information from these detector arrays is processed to calculate the refractive index of a sample placed in operative association with the optical means of the instrument.

FIG. 8 shows the electronic circuitry of refractometer 10 in block diagram format. The circuitry includes a power control circuit 90 connected to a central processing unit 92 and also to illumination LED array 43 and position light source 86. CPU 92 is linked via an address/data bus 94 to other circuitry and electronic input and output devices of refractometer 10. Data communication with peripheral devices, such as a personal computer, is possible through serial ports 22 each connected to data bus 94 by a universal asynchronous receiver/transmitter 96. User interface 16 includes a keypad input 100 surrounding a liquid crystal display 102 and having the following command buttons shown in FIG. 1: MENU button 104, READ button 106, Down button 108, Up button 110, and SELECT button 112. Memory blocks include a 128 kilobyte static random access memory (SRAM) 114 for storing program variables that do not need to be saved when the instrument is switched off; a 256 kilobyte flash electrically erasable programmable read-only memory (EEPROM) 116 for storing executable code and sucrose conversion factors provided by the International Commission for Uniform Methods of Sugar Analysis; and a 32 kilobyte EEPROM 118 for storing changeable user settings, calibration data, and customizable conversion tables (custom channels). A real-time clock 120 provides measurement time and date information for laboratory records. Reading measurement information, including a temperature value from a temperature sensor 126 associated with prism assembly 24 and signal information from the array elements of position detector 88 and shadowline detector 66, is controlled by a programmable timer circuit 124 and a programmable logic circuit 128. As described above, position detector 88 is optically coupled to position light source 86. Analog signal information from each scan of position detector 88 is input to a low pass filter 130 followed by an analog-to-digital converter 132. Likewise, shadowline detector 66 is optically coupled to LED array 45, and analog signal information from each scan of shadowline detector 66 is input to a low pass filter 134 and then an analog-to-digital converter 136.

As a possible optional feature, a stepper motor 138 can be operatively coupled to elevator arm 80 to provide automatic positioning of movable optical element 50 as opposed to manual positioning using shadowline adjustment knob 20.

It will be recalled that signal information from position detector 88 and shadowline detector 66 describe the refractive optical system. More specifically, light from position source 86 strikes position detector 88 at a location depending upon the position of movable optical element 50, and light transmitted by the sample illuminates shadowline detector 66 to define a shadowline at a location depending upon the position of movable optical element 50 and the index of refraction of the sample. The location at which light from position light source 86 strikes position detector 88 is expressed in terms of a cell number CN1. The location of the shadowline on shadowline detector 66 is specified in terms of a cell number CN2 at which a dark area on the shadowline detector transitions to an illuminated area.

Figure 9:
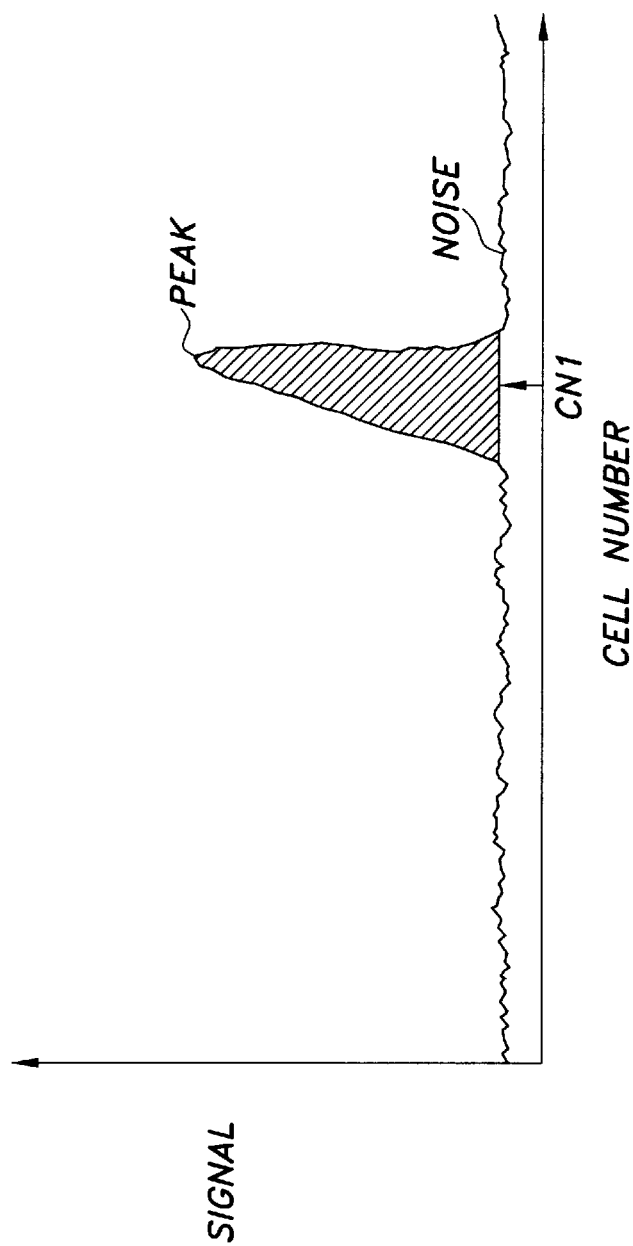
FIG. 9 is a graph of signal intensity as a function of cell number for a typical scan of a position detector of the refractometer.

FIG. 9 shows a typical plot of signal intensity as a function of cell number for a scan of position detector 88. Since the position light source 86 and aperture 92 define a slit source, a reasonably well-defined peak appears on the detector array. In a currently useful scheme, the peak cell is registered and the noise level is determined by moving down each side of the spike until an increase in amplitude is once again found. The fulcrum point of the shaded area beneath the spike and above the noise level is then determined and the corresponding cell number or fractional cell number is chosen as CN1.

Figure 10:
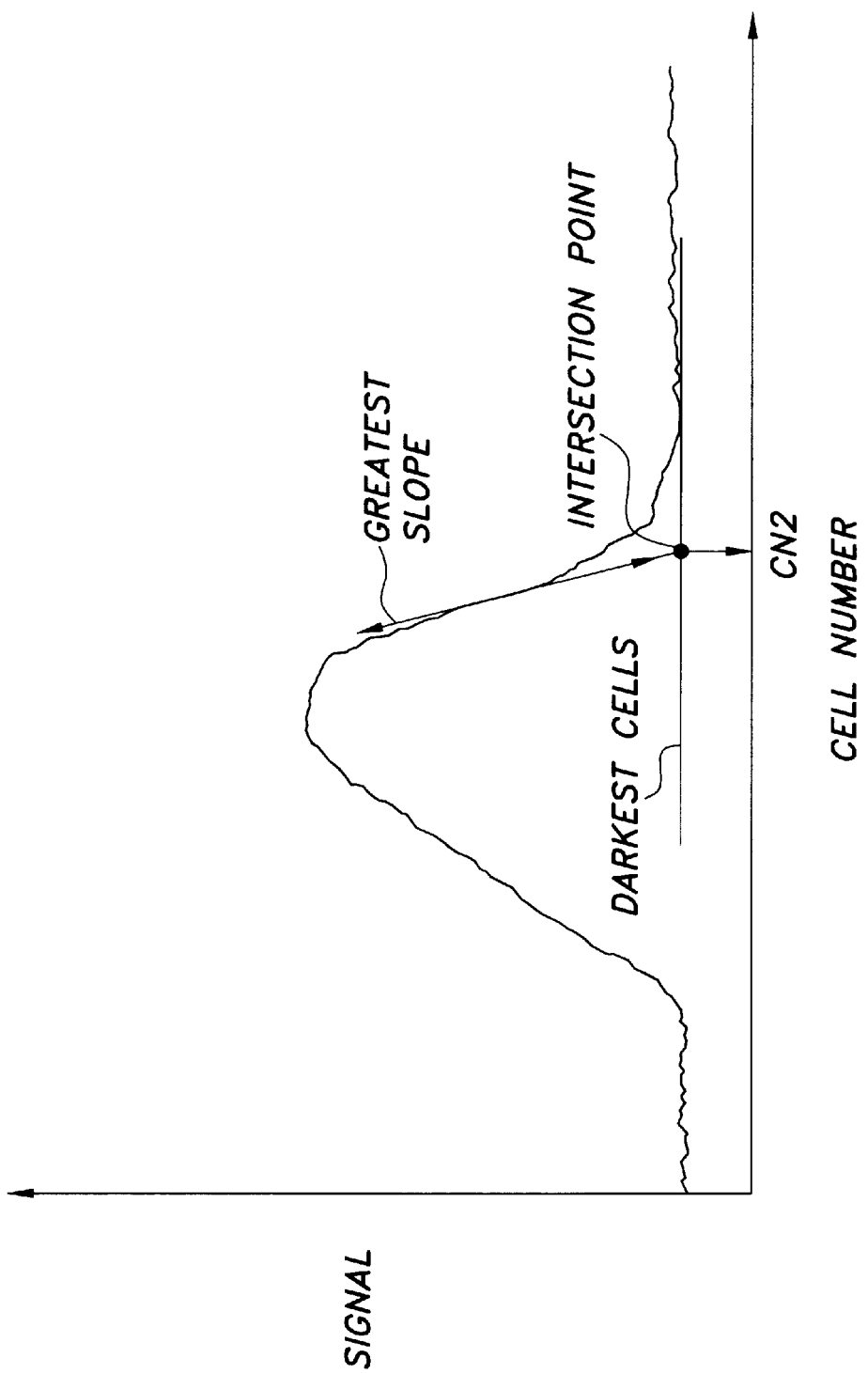
FIG. 10 is a graph of signal intensity as a function of cell number for a scan of a shadowline detector of the refractometer.

Determination of CN2 is illustrated with reference to FIG. 10, which shows a typical plot of signal intensity as a function of cell number for a scan of shadowline detector 66. Here, there is a transition from light to dark spread out across many cells on the detector array. A suitable scheme for arriving at CN2 includes registering a peak cell, moving downward along to the right side of the peak cell until the greatest slope is found between successive cells, finding the dimmest cells to the right of the peak cell to establish a "dark" line, finding an intersection point between the greatest slope line and the dark line, and choosing CN2 as the cell number or fractional cell number corresponding to the intersection point.

Figure 11A:
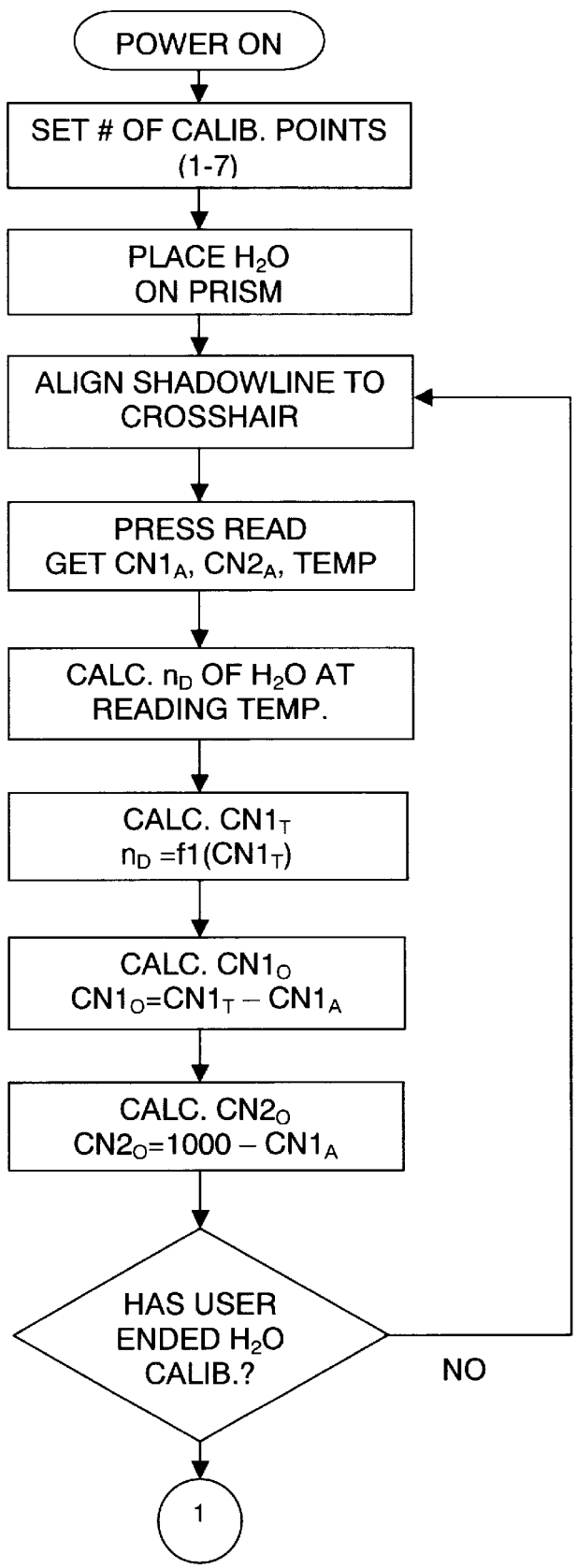
FIGS. 11A–11C form a schematic flow diagram showing operational logic of the refractometer of the present invention.
Figure 11B:
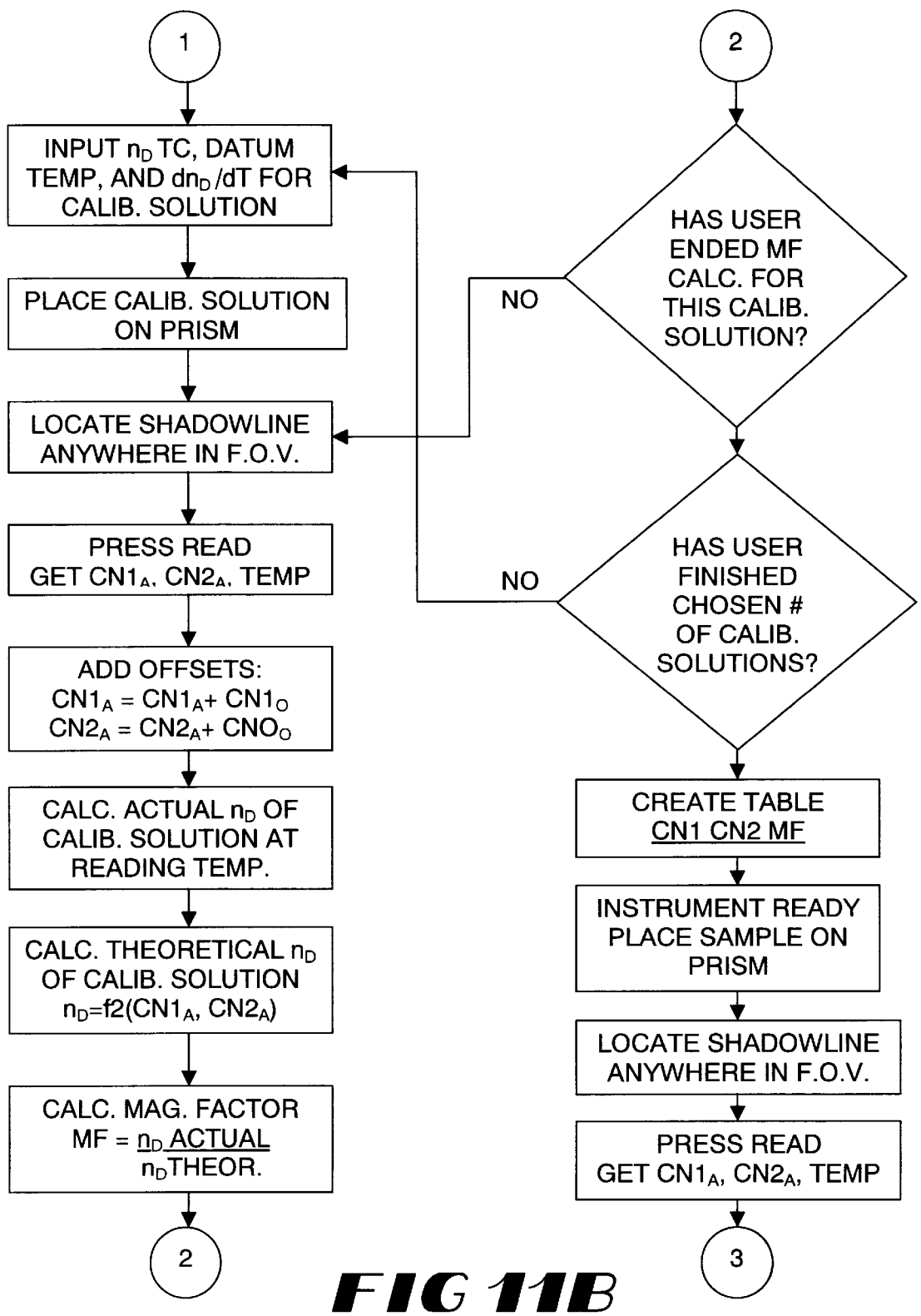
Figure 11C:
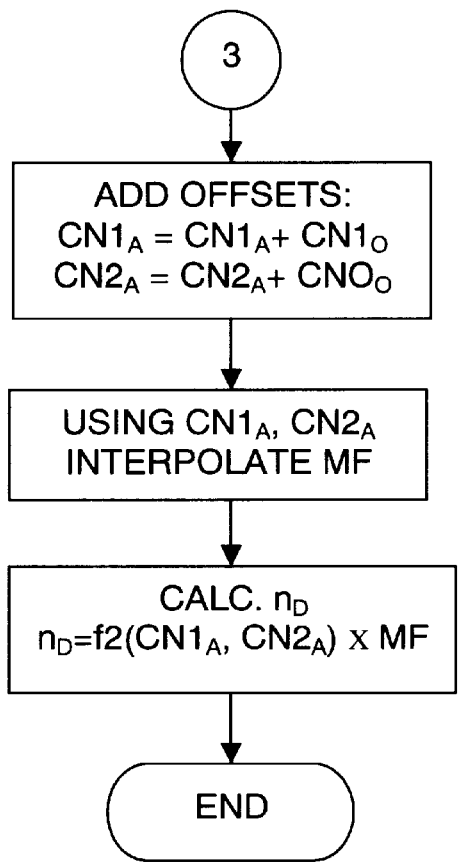

The flowchart of FIGS. 11A–11C illustrates the operational logic steps for calibrating refractometer 10 and using the refractometer to measure the refractive index of a sample. Calibration generally involves two stages. In the first stage, distilled water is used as a calibration fluid to ascertain how much the actual instrument's optical components vary from those of a "nominal instrument" and establish offset values. In the second stage of calibration, a series of calibration fluids are used to establish localized magnification factors for adjusting computed measurement values.

Before the flowchart is referenced, it is necessary to describe a relational function pre-programmed into flash EEPROM 116. Function f(CN1, CN2) is the relationship between refractive index $n_D$, CN1, and CN2. Accordingly:

$$n_D = f(CN1, CN2).$$

Function f(CN1, CN2) can be stored as a table of values $n_D$, CN1, and CN2 for a range of samples having known refractive indices and a range CN2 values adjusted in intervals over the cell range representing the field of view of shadowline detector 66. For example, the field of view of shadowline detector 66 in the preferred embodiment is generally from cell 750 to cell 1250, with cell 1000 representing the crosshair reference intersection. Consequently, the shadowline is adjusted to appear at cell number 750 (CN2) and a set of measurements are taken to determine CN1 values corresponding to known indices of refraction, the shadowline is then adjusted by a 50 cell step to cell number 800 and the set of measurements are repeated to determine CN1 values corresponding to known indices of refraction, and so on until CN1=1250 is completed.

With refractometer turned on, the operator uses the keypad input 100 to select the calibration menu option, and then selects the number of calibration points from one to seven (six calibration oils and water) from a displayed list of choices. The display then shows a calibration screen which prompts the operator through a complete calibration. First, the operator places distilled water directly on refraction prism surface 26A and closes illumination prism 30 over the sample, and then the operator rotates shadowline adjustment knob 20 to align the shadowline to the crosshair reference seen through eyepiece 14. At this point, the operator commences a reading by pressing the READ button 106, and actual values $CN1_A$, $CN2_A$, and temperature are obtained as described previously. The true refractive index of water at the reading temperature is calculated using stored temperature compensation data, and a theoretical value $CN1_T$ is computed for using the temperature compensated index of refraction of water and the function f. Thus, an offset $CN1_O$ representing the difference between the expected or theoretical $CN1_T$ and the actual $CN1_A$ can be calculated. A similar offset $CN2_O$ is computed for by assuming $CN2_T$ is equal to cell 1000 at the crosshair, and subtracting the actual $CN2_A$ therefrom.

Once the operator has completed water calibration to his or her satisfaction to establish offsets for CN1 and CN2, the second stage of calibration is begun as illustrated in FIG. 11B. The user is prompted to input index of refraction information for the calibration solution to permit a temperature compensated index to be computed. With the calibration solution set between prisms 26 and 30, the operator manually turns adjustment knob 20 to locate the shadowline anywhere in the field of view of eyepiece 14 and then presses READ button 106. The actual cell number values from the reading are adjusted by their respective offsets. The index of refraction of the calibration solution at the reading temperature is computed using the information previously input by the operator, and then a theoretical value of the index is computed by inputting the actual cell numbers (as offset) in the functional relationship f2, interpolating if necessary. The magnification factor is simply the actual or true index divided by the theoretically derived index. Once the operator has completed all calibration solutions, a table of CN1, CN2, and magnification factor MF is stored.

Following calibration to establish offsets and magnification factors, refractometer 10 is ready for operation in its automatic mode. With the sample between prisms 26 and 30, the shadowline can be located anywhere in the field of view of eyepiece 14 by turning shadowline adjustment knob 20. The operator presses read to get cell number values, and the stored offsets from calibration are added thereto. Using the cell numbers as offset, a magnification factor is interpolated from the magnification factor table stored during the second phase of calibration. The index of refraction is then calculated using the relationship f2 and the interpolated magnification factor.

As an alternative approach to using the functional relationship described above, it is also possible to establish a functional relationship between refractive index and CN1 alone by assuming CN2=1000, and then determine to what extent CN1 must be adjusted before calculation of refractive index to account for CN2 being "off center" (either greater than or less than 1000).

Measurement output is reported by LCD display 102, and can be downloaded to peripheral devices through serial ports 22. Readings can be reported in refractive index, percent solids, temperature compensated refractive index, and temperature compensated percent solids, depending upon operator selection.

It will be recognized that the present invention allows for better repeatability of measurements by removing human error associated with visually aligning the shadowline to the crosshairs prior to taking a sample reading. Due to the use of first and second detection paths, the present invention is also capable of operating in a manual mode if desired. Moreover, the adjustability of movable optical element 50, coupled with the ability of the instrument to take readings with the shadowline located anywhere within the field of view of eyepiece 14, gives refractometer 10 a very large number of ranges for custom applications.

What is claimed is:

1. A transmitted light refractometer comprising:
   optical means for receiving light transmitted by a sample placed in operative association with said optical means to define an illumination boundary shadowline;
   a beam splitter for projecting said shadowline along first and second detection paths;
   an eyepiece on said first detection path for presenting an image of said shadowline to an operator;
   a light-sensitive detector on said second detection path for generating signal information indicative of a location of said shadowline on said light-sensitive detector, said location being dependent upon the index of refraction of said sample; and processing means for evaluating said signal information to calculate the index of refraction of said sample.

2. A transmitted light refractometer according to claim 1, wherein said optical means includes a movable optical element before said beam splitter for acquiring said shadowline and redirecting said shadowline to said beam splitter, and position sensing means for generating position signal information indicative of a position of said movable optical element, wherein said processing means evaluates said signal information from said light-sensitive detector and said position signal information to calculate the index of refraction of said sample.

3. A transmitted light refractometer according to claim 2, wherein said movable optical element is a mirror.

4. A transmitted light refractometer according to claim 2, wherein said light-sensitive detector is a linear scanned array.

5. A transmitted light refractometer according to claim 2, wherein said position sensing means includes a position light source and a light-sensitive position detector cooperating with said position light source, one of said position light source and said position detector being mounted for travel with said movable optical element relative to the other of said position light source and said position detector.

6. The transmitted light refractometer according to claim 5, wherein said position light source is mounted for travel with said movable optical element.

7. A refractometer comprising:

optical means for receiving light from a sample placed in operative association with said optical means to define an illumination boundary shadowline, said optical means including a movable optical element for acquiring said shadowline and redirecting said shadowline along a detection path;

position sensing means for generating position signal information indicative of a position of said movable optical element;

a light-sensitive detector on said detection path for generating signal information indicative of a location of said shadowline on said light-sensitive detector, said location being dependent upon the index of refraction of said sample and the position of said movable optical element; and processing means for evaluating said position signal information and said signal information generated by said light-sensitive detector to determine the index of refraction of said sample.

8. The refractometer according to claim 7, further comprising a beam splitter for dividing said detection path, and an eyepiece and a reticle arranged after said beam splitter to present a viewable image of said shadowline relative to a reference marking.

\* \* \* \* \*

UNITED STATES PATENT AND TRADEMARK OFFICE
Certificate

Patent No. 6,172,746                                                Patented: January 9, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Erin D. Spring, Corfu; Michael J. Byrne, East Aurora; Thomas E. Ryan, Batavia; Kyle R. Bleyle, Keshav D. Sharma, both of Lancaster; Robert C. Atkinson, Buffalo; and David J. Cash, Kenmore, all of NY.

Signed and Sealed this Thirteenth Day of August 2002.

<div align="right">

FRANK G. FONT
*Supervisory Patent Examiner*
Art Unit 2877

</div>